(12) United States Patent
Takagi et al.

(10) Patent No.: US 7,351,225 B2
(45) Date of Patent: Apr. 1, 2008

(54) SAFETY INDWELLING NEEDLE

(75) Inventors: Nobuo Takagi, Osaka (JP); Masahisa Tanimoto, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/398,607

(22) Filed: Apr. 6, 2006

(65) Prior Publication Data

US 2006/0184116 A1    Aug. 17, 2006

Related U.S. Application Data

(62) Division of application No. 11/065,579, filed on Feb. 25, 2005, now abandoned.

(30) Foreign Application Priority Data

Feb. 26, 2004   (JP)   ............................... 2004-51028
Feb. 26, 2004   (JP)   ............................... 2004-51029

(51) Int. Cl.
*A61M 5/00* (2006.01)
(52) U.S. Cl. .................................................... 604/110
(58) Field of Classification Search ............... 604/110, 604/167.01, 187, 192, 197–198, 263, 164.01, 604/164.08
See application file for complete search history.

(56) References Cited

U.S. PATENT DOCUMENTS 5,336,199 A * 8/1994 Castillo et al. ............. 604/198
5,419,766 A * 5/1995 Chang et al. ............... 604/110
5,772,636 A * 6/1998 Brimhall et al. ............ 604/198
5,830,190 A   11/1998 Howell ....................... 604/168
6,616,630 B1   9/2003 Woehr et al. ................ 604/110
2002/0026154 A1* 2/2002 Chang ......................... 604/198
2003/0163095 A1* 8/2003 Nakashima .................. 604/263

FOREIGN PATENT DOCUMENTS

| EP | 0 645 159 A1 | 3/1995 |
| JP | 2002-102345 A | 4/1992 |
| JP | 7-148270 A | 6/1995 |
| JP | 7-328116 A | 12/1995 |
| JP | 07328116 | * 12/1995 |
| JP | 10-52499 A | 2/1998 |

\* cited by examiner

*Primary Examiner*—Kevin C. Sirmons
*Assistant Examiner*—Catherine N. Witczak
(74) *Attorney, Agent, or Firm*—Kubovcik & Kubovcik

(57) ABSTRACT

There is provided a safety indwelling needle comprising an inner needle unit 1 having an inner needle 11, an inner needle hub 13 provided on a proximal end of the inner needle 11 and a needle protecting member disposed at a distal side of the inner needle hub 13, and an outer needle unit 2 having an outer needle 21, characterized in that the needle protecting member includes an extendable housing unit 31 and the housing unit 31 can partly store the inner needle 11 therein in a state where the housing unit 31 is extended.

4 Claims, 8 Drawing Sheets

SAFETY INDWELLING NEEDLE

This application is a divisional of U.S. patent application Ser. No. 11/065,579 filed Feb. 25, 2005, abandoned, which claims priority of Japanese Patent Application Nos. 2004-51028 and 2004-51029 filed Feb. 26, 2004, which are incorporated herein by reference.

BACKGROUND OF THE INVENTION

The present invention relates to an indwelling needle assembly to be used for fluid infusion, hemodialysis, and the like. More specifically, the present invention relates to a safety indwelling needle provided with a safety mechanism.

In recent years, a risk of transmission of AIDS, hepatitis virus or the like to medical personnel caused by accidental puncture by a pointed edge of an injection needle or the like, contaminated by blood has been emerging as a problem. Therefore, a safety indwelling needle for an indwelling needle assembly having an inner needle and an outer needle, which prevents accidental puncture by covering an inner needle after use without putting a cap again thereon, has been invented. For example, there is disclosed a safety indwelling needle in which an inner needle is retracted and stored in a needle cover with a spring by pressing a button provided on the indwelling needle after puncture (for example, Japanese Patent Laid-Open No. 52499/1998).

Also, there is disclosed a safety indwelling needle in which a spring-type needlepoint protecting means is disposed within an outer needle hub, and when the inner needle is pulled out, the needlepoint protecting means comes apart from the outer needle hub to cover an extremity of the inner needle (for example, Japanese Patent Laid-Open No. 102345/2002).

Furthermore, there is disclosed a safety indwelling needle characterized in that a sliding cover provided on an inner needle is extended and the entire needle is stored therein when the inner needle is pulled out from an outer needle (for example, Japanese Patent No. 3400550 and Japanese Patent Laid-Open No. 148270/1995).

In the safety indwelling needles provided with a safety mechanism in the related art, the needlepoint protecting means for covering the inner needle pulled out from an outer needle unit is required to have a size that affords enough space for accommodating the entire inner needle, and hence the size of the indwelling needle itself is significant. Also, the safety indwelling needle including a spring as a needlepoint protecting means has a problem such that a force required for pulling the inner needle increases because a friction between the inner needle and the needlepoint protecting means increases by an urging force of the spring, whereby the usableness is deteriorated. Also, in the safety indwelling needle having a needlepoint protecting means for storing the entire inner needle by a sliding cover, there is a problem such that shortening of the length of the sliding member in a constricted state is limited, and the structure becomes complicated by shortening the same.

SUMMARY OF THE INVENTION

In view of such circumstances, it is an object of the present invention to provide a safety indwelling needle to be used for fluid infusion, hemodialysis and the like, which is provided with an accidental puncture preventing measure and has a compact and simple structure with greater usableness.

In other words, the present invention relates to a safety indwelling needle comprising an inner needle unit having an inner needle, an inner needle hub provided on a proximal end of the inner needle and a needle protecting member disposed at a distal side of the inner needle hub, and an outer needle unit having an outer needle, characterized in that the needle protecting member includes an extendable housing unit and the housing unit can partly store the inner needle in a state that the housing unit is extended.

A safety indwelling needle according to the present invention is configured to store a predetermined length of an inner needle including an extremity thereof in a needle protecting member by pulling out an inner needle unit. A compact safety indwelling needle is obtained because the needle protecting member has an extendable housing unit which can partly store the inner needle and is smaller than a conventional indwelling needle. Besides, possibility of re-projection of the extremity of the inner needle from the needle protecting member is eliminated by preventing a constriction of the housing unit after the inner needle is stored.

DESCRIPTION OF THE DRAWINGS

The safety indwelling needle of the present invention is described in detail below by referring to preferable embodiments shown in the appended drawings. However, the present invention is not limited to these embodiments.

Within the description of the embodiments, a side toward a medical professional during operation is referred to as a proximal side, and a side toward a patient is referred to as a distal side. Also, especially in an explanation of an end portion of structural elements, an end of the element on the side of the medical professional is referred to as a proximal end and an end of the element on the side of the patient is referred to as a distal end.

DETAILED DESCRIPTION OF THE INVENTION

First Embodiment

Figure 1:
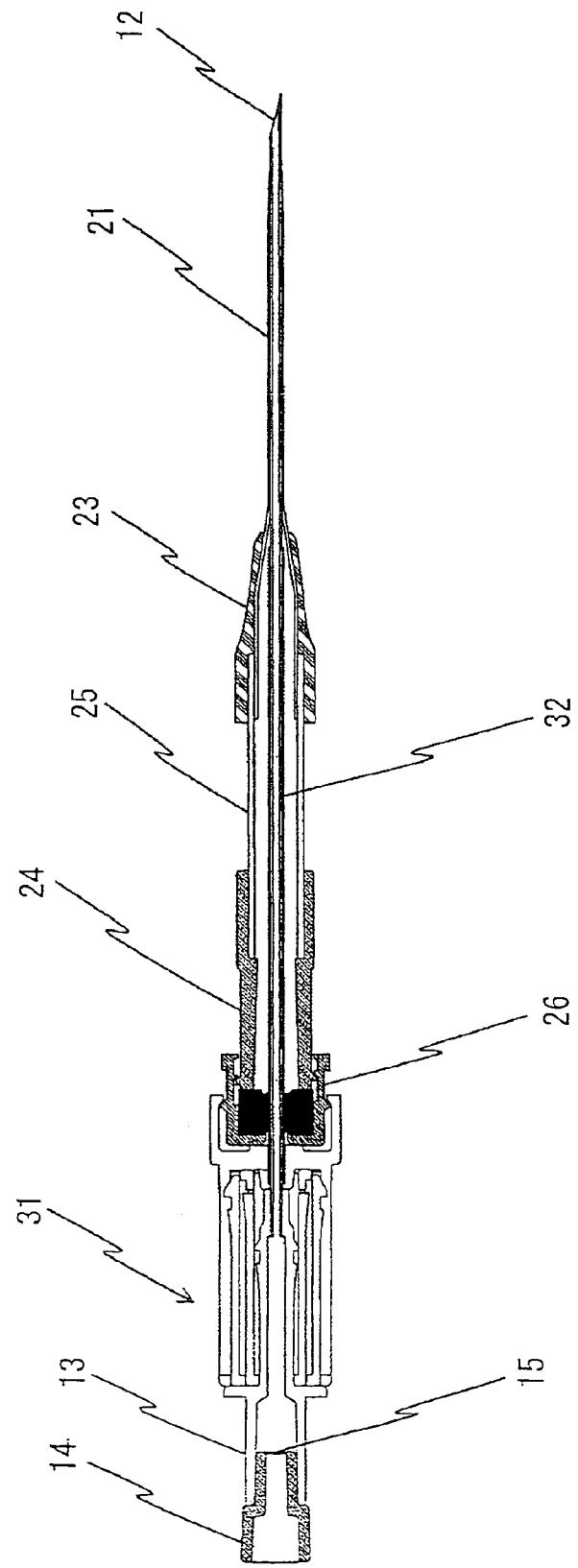
FIG. 1 is a cross-sectional view of the safety indwelling needle according to an embodiment of the present invention before use.
Figure 2:
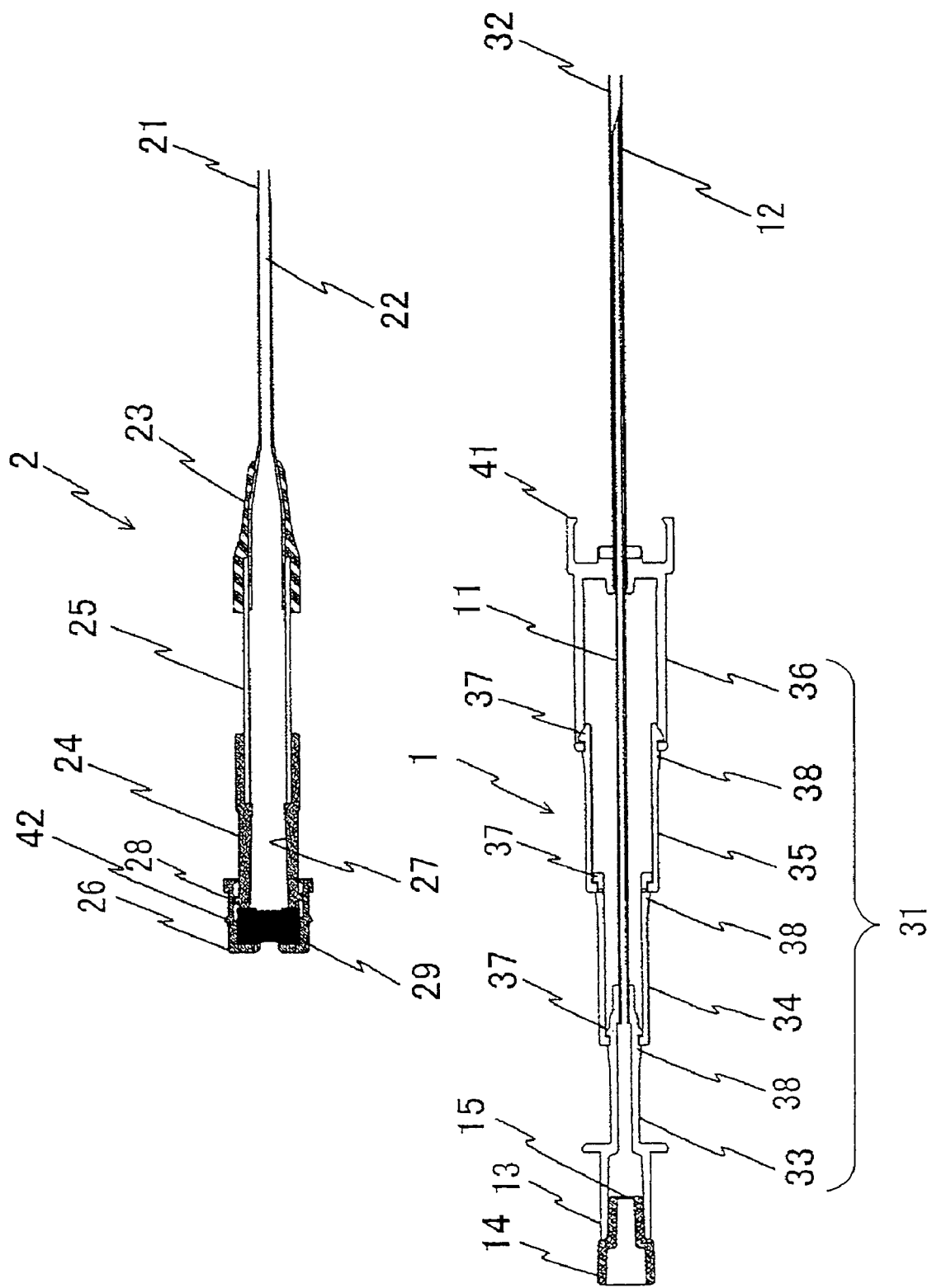
FIG. 2 is a cross-sectional view of the safety indwelling needle shown in FIG. 1 after pulling out an inner needle unit.

The safety indwelling needle according to a first embodiment shown in FIG. 1 and FIG. 2 is used as an indwelling needle especially suitable for a blood purifying treatment such as artificial dialysis.

The safety indwelling needle shown in FIGS. 1 and 2 includes an inner needle unit 1 and an outer needle unit 2. The inner needle unit 1 includes an inner needle 11 having a sharp needlepoint 12 at a distal end of the inner needle 11 and an inner needle hub 13 at a proximal end of the inner needle 11, and an inner needle cap 14 attached to the inner needle hub 13.

As a needle protecting member, a housing unit 31 includes a first housing member 33, a second housing member 34, a third housing member 35 and a fourth housing member 36, and a needle covering member 32 for storing and covering the needlepoint 12 which is a distal end of the inner needle 8. The housing unit 31 is extended and covers a distal end of the inner needle 11 of the inner needle unit 1 when the inner needle 1 is pulled out from the outer needle unit 2. In the present embodiment, the first housing member 33 and the inner needle hub 13 are formed integrally.

The outer needle unit 2 includes an outer needle 21 having a lumen 22, an outer needle hub 23, an outer needle connector 24, a tube 25 having flexibility for connecting the outer needle hub 23 and the outer needle connector 24 and an outer needle cap 26.

The outer needle 21 of the outer needle unit 2 is preferably one having a hollow shape and suitable flexibility. A preferred material for the outer needle 21 is a soft resin such as ethylene-tetrafluoroethylene co-polymer (ETFE), polyurethane, a polyether-nylon resin, polypropylene or the like. The outer needle 21 may partly or entirely provide visibility of the interior. It is also possible to blend a contrast medium for X-ray, such as barium sulfate, barium carbonate or the like, to the material of the outer needle 21 for providing a radiographic function.

The distal end of the outer needle 21 is preferably formed into a tapered shape in which an outer diameter is gradually reduced toward the distal end for allowing puncture of a skin of a living body to be easily performed in a less invasive manner. It is also possible to provide one or more holes in a vicinity of the distal end of the outer needle 21 so as to allow liquid flowing inside of the outer needle 21 to efficiently come in and out.

The outer needle hub 23 is attached to the outer needle 21 at the proximal end thereof in a liquid-tight manner, and the lumen 22 of the outer needle 21 and an interior of the outer needle hub 23 communicate with each other. The outer needle hub 23 is connected to the tube 25, and the tube 25 is connected to the outer needle connector 24 having a female luer taper 27 therein to be connected to a separate medical instrument. The outer needle connector 24 may have a locking means 28 on an outer periphery of the outer needle connector 24 at a proximal end thereof for connecting the outer needle unit 2 to the separate medical instrument. The separate medical instrument may also be connected to the tube 25 by using flexibility of the tube 25 without providing the outer needle unit with the outer needle connector 24.

The outer needle connector 24 is provided with the outer needle cap 26 fitted thereon. Also, the outer needle cap 26 is provided therein with a packing 29 having resiliency that enables the inner needle 11 to penetrate therethrough. The packing 29 closes a through hole made by the inner needle 11 after removal thereof, so that liquid is prevented from flowing out from a proximal end of the outer needle unit 2.

Also, as shown in FIG. 1, the fourth housing member 36 provided in the inner needle unit 1 is detachably connected to the outer needle cap 26. The connecting means between the outer needle cap 26 and the fourth housing member 36 is not specifically limited. The housing unit 31 is extended while being connected to the outer needle cap 26 when the inner needle unit 1 is pulled out from the outer needle unit 2. When the housing unit 31 reaches a maximally extended state by first stoppers 37 provided on the respective housing members 33-35, the fourth housing member 36 comes off from the outer needle cap 26 by further pulling the inner needle unit 1.

For example, the fourth housing member 36 is detachably connected to the outer needle cap 26 by engaging a flexible hook-shaped member 41 provided on the fourth housing member 36 with a projecting portion 42 provided on the outer needle cap 26. Alternatively, the hook-shaped member may be provided on the outer needle cap 26 and the projecting portion may be provided on the fourth housing member 36.

The inner needle 11 is a hollow needle. The material of the inner needle 11 may be, for example, stainless steel, aluminum, aluminum alloy, titanium or titanium alloy. In view of processability and cost, stainless steel is preferably used for the inner needle 11. The inner needle 11 is formed with the sharp needlepoint 12 at the distal end thereof. The shape of the needlepoint 12 is not specifically limited, but in the present embodiment, the needlepoint 12 includes a cutting surface inclined from an axis of the inner needle 11 by a predetermined angle.

The inner needle unit 1 is inserted into a cavity of the outer needle unit 2. The housing unit 31 through which the inner needle 11 passes is interposed between a distal end of the inner needle hub 13 and a proximal end of the outer needle cap 26 so as to be detachably connected to the proximal end of the outer needle cap 26. The proximal end of the inner needle 11 is secured to a distal end of the first housing member 33 in a liquid-tight manner, and a lumen of the inner needle 11 communicates with an internal space of the first housing member 33 and the inner needle hub 13. The inner needle hub 13 is constructed of a substantially cylindrical hollow member. The means of fixing the inner needle 11 and the housing member 33 may be, for example, fitting, caulking, fusion bonding, or adhesion by an adhesive agent or the like, or a combination of these means. Furthermore, the inner needle hub 13 is preferably transparent, colored transparent or translucent so that the interior of the inner needle hub 13 is visible for observing flashback of blood.

The inner needle hub 13 may be provided with a ventilation filter 15 on a proximal end thereof. Alternatively, as shown in FIG. 1, the inner needle cap 14 provided with the ventilation filter 15 may be attached on the proximal end of the inner needle hub 13. The ventilation filter 15 has a characteristic that it transmits gas but blocks liquid. For example, various sintered porous members, a hydrophobic non-woven fabric or other porous members may be employed as the ventilation filter 15. The sintered porous member is preferably one obtained by sintering a powdered polymer material such as polyethylene and a material containing hydrophilic, water soluble or water-swelling polymer. The ventilation filter 15 using such a sintered porous member can prevent air from the outside from contacting with a liquid such as blood.

As shown in FIG. 2, the needle protecting member according to the present embodiment includes the housing unit 31 having the first to fourth housing members 33-36 and the needle covering member 32.

The housing unit 31 is extended by pulling out the inner needle unit 1 from the outer needle unit 2. The inner needle 11 can slide relative to the needle covering member 32, and the distal end portion of the inner needle 11 including the needlepoint 12 is thereby covered by the needle covering member 32. Also, the proximal end portion of the inner needle 11 is covered by the extended housing unit 31. Therefore, the inner needle 1 is entirely covered by the extended housing unit 31 and the needle covering member 32.

When the housing unit 31 is extended to a maximum extended state by the first stoppers 37, the housing unit 31 is fixed by second stoppers 38 provided on the respective housing members 33-36 so as not to be constricted. When the inner needle unit 1 is further pulled out in this state, the inner needle unit 1 and the outer needle unit 2 are separated as shown in FIG. 2. The housing members 33-36 of the housing unit 31 may be provided with a stopper (not shown) which maintains the state in which the housing unit 31 is constricted and allows the housing member 31 to extend only when the housing member 31 is pulled by a force of a certain degree.

Although the housing unit 31 is composed of a combination of hollow members being different in diameter, that is, the first to fourth housing members 33-36, in FIG. 2, the number of the housing members is not limited. The axial length of the housing unit 31 in the constricted state can be shortened by increasing the number of the housing members. However, employing too many housing members is not preferable because the structure or the housing unit 31 becomes complicated and an outer diameter of the housing unit 31 increases too much. In contrast, when the number of the housing members is reduced, the structure of the housing unit 31 is simplified. However, a total length of the housing unit 31 in a state of being constricted cannot be shortened, thereby the total length of the safety indwelling needle increases.

Although the housing members which are increased in diameter toward a distal end are disposed in FIG. 2, housing members which are decreased in diameter toward the distal end may be used.

As shown in FIG. 1, the needle covering member 32 is inserted into an internal space of the outer needle unit 2 when the inner needle unit 1 and the outer needle unit 2 are assembled before use. The length of the needle covering member 32 is preferably such that a distal end of the needle covering member 32 extends to the vicinity of an extremity within the outer needle hub 23 in a state before use as shown in FIG. 1. Although the shape of the needle covering member 32 is not specifically limited, it is preferably a cylindrical-shape having an inner diameter substantially same as an outer diameter of the inner needle 11. The material of the needle covering member 32 may be, for example, stainless steel, aluminum, aluminum alloy, titanium or titanium alloy. However, in view of processability and cost, stainless steel is preferably used. The needlepoint 12 of the inner needle 11 formed of metal can be reliably covered by using metal material for the needle covering member 32.

After the safety indwelling needle shown in FIG. 1 is punctured into a body, the inner needle unit 1 is pulled out from the outer needle unit 2 to obtain the state shown in FIG. 2. At this time, the housing unit 31 having the fourth housing member 36 is connected to the outer needle cap 26 of the outer needle unit 2. Accordingly, as the inner needle unit 1 is pulled out from the outer needle unit 2, the housing unit 31 is extended. When the needlepoint 12 of the inner needle 11 of the inner needle unit 1 is pulled out until it occupies the internal space of the outer needle unit 2, the needlepoint 12 of the inner needle 11 is covered by the needle covering member 32 provided on the fourth housing member 36 of the inner needle unit 1. When the housing unit 31 is extended to the maximum extended state defined by the first stoppers 37, connection between the fourth housing member 36 and the outer needle cap 26 is released by the inner needle unit 1 being further pulled, whereby the inner needle unit 1 and the outer needle unit 2 are separated as shown in FIG. 2.

The entire inner needle 11 including the needlepoint 12 of the separated inner needle unit 1 is covered by the extended housing unit 31 and the needle covering member 32, and the inner needle unit 1 can be safely discarded. Also, because the extended housing unit 31 is prevented from constricting again by the second stoppers 38 provided on the respective housing members 33-36 of the housing unit 31, the needlepoint 12 does not become exposed again, whereby the inner needle unit 1 can be further safely discarded.

Second Embodiment

Figure 3:
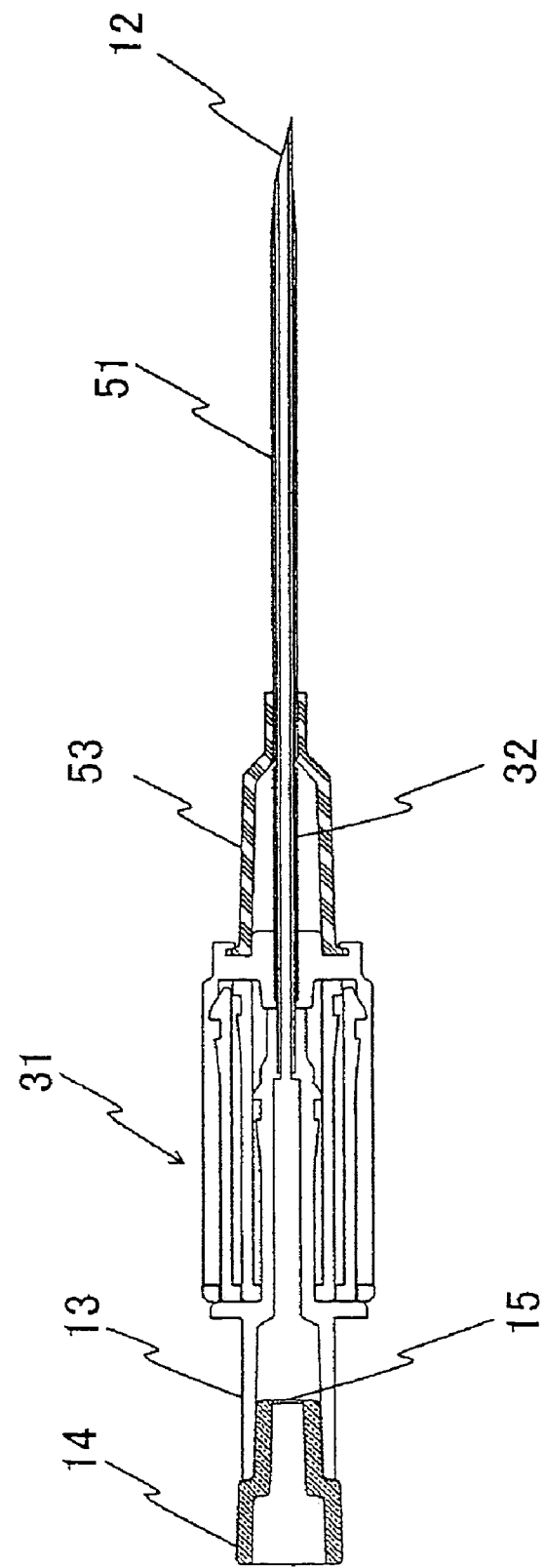
FIG. 3 is a cross-sectional view of the safety indwelling needle according to another embodiment of the present invention before use.
Figure 4:
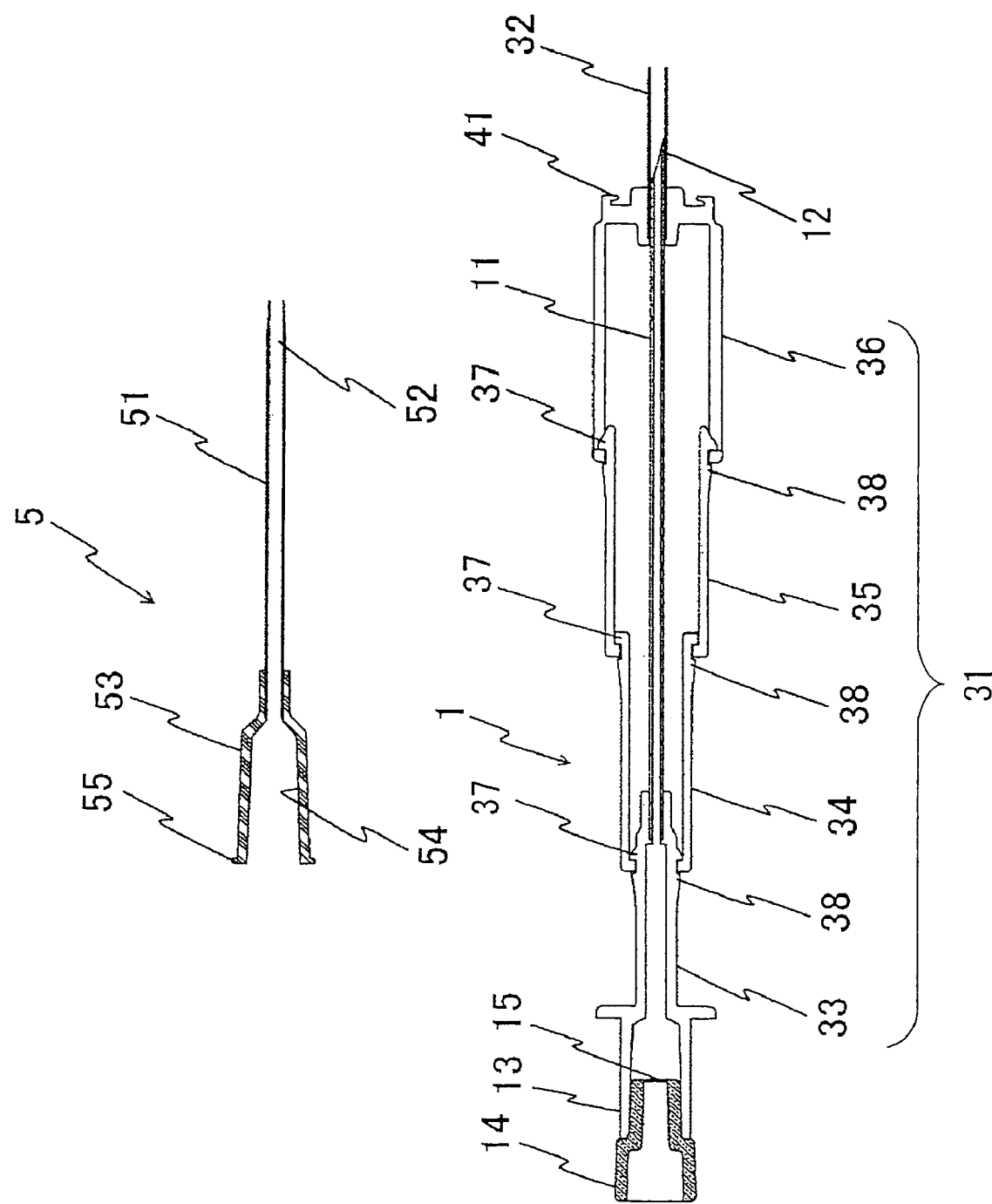
FIG. 4 is a cross-sectional view of the safety indwelling needle shown in FIG. 3 after pulling out an inner needle unit.

The safety indwelling needle according to a second embodiment shown in FIG. 3 and FIG. 4 is mainly used as an indwelling needle for fluid infusion and the like. In FIGS. 3 and 4, a structural element of the safety indwelling needle of the second embodiment, which is the same as a structural element of the safety indwelling needle of the first embodiment, is respectively identified using the same reference number as in FIGS. 1 and 2.

The safety indwelling needle shown in FIGS. 3 and 4 includes the inner needle unit 1 which is substantially the same as the inner needle unit 1 of the first embodiment and an outer needle unit 5. The outer needle unit 5 includes an outer needle 51 having a lumen 52 and an outer needle hub 53.

The outer needle 51 of the outer needle unit 5 is employed the same as the outer needle 2 of the outer needle unit 2 of the first embodiment. The outer needle hub 53 is attached to the outer needle 51 at a proximal end thereof in a liquid-tight manner, and a lumen 52 of the outer needle 51 and an interior of the outer needle hub 53 communicate with each other. The outer needle hub 53 is preferably formed with a female luer taper 54 at an inner surface thereof so as to be capable of connecting with a medical instrument such as an fluid infusion set or a syringe. The outer needle hub 53 may have a locking means 55 on an outer periphery of the proximal end so as to allow connection of a separate medical instrument to the outer needle hub 53.

As shown in FIG. 3, the fourth housing member 36 provided on the inner needle unit 1 is detachably connected to the outer needle hub 53. The connecting means between the outer needle hub 53 and the fourth housing member 36 is the same as the connecting means between the outer needle cap 26 and the fourth housing member 36 in the first embodiment. In the case that the outer needle hub 53 is detachably connected to the fourth housing member 36 by engaging the hook-shaped member 41 to a projecting portion as described in the first embodiment, the projecting portion may be the locking means 55 provided on the outer needle hub 53.

The inner needle unit 1 is inserted into a cavity of the outer needle unit 5, and the housing unit 31 through which the inner needle 11 passes is interposed between a distal end of the inner needle hub 13 and a proximal end of the outer needle hub 53, and is detachably connected to the proximal end of the outer needle hub 53.

As shown in FIG. 3, when the inner needle unit 1 and the outer needle unit 5 are assembled before use, the needle covering member 32 is inserted into an internal space of the outer needle unit 5. The length of the needle covering member 32 is preferably such that a distal end of the needle covering member 32 extends to a vicinity of an extremity within the outer needle hub 53 before using the safety indwelling needle as shown in FIG. 3.

After the safety indwelling needle shown in FIG. 3 is punctured into the skin of a body, the inner needle unit 1 is pulled out from the outer needle unit 5 to obtain the state shown in FIG. 4. At this time, the housing unit 31 having the fourth housing member 36 is connected to the outer needle hub 53. Accordingly, as the inner needle unit 1 is pulled out from the outer needle unit 5, the housing unit 31 is extended. When the needlepoint 12 of the inner needle 11 of the inner needle unit 1 is pulled out until it occupies the internal space of the outer needle unit 5, the needlepoint 12 of the inner needle 11 is covered by the needle covering member 32 provided on the fourth housing member 36 of the inner needle unit 1. When the housing unit 31 is extended to the maximum extended state defined by the first stoppers 37, connection between the fourth housing member 36 and the outer needle hub 53 is released by the inner needle unit 1 being further pulled, whereby the inner needle unit 1 and the outer needle unit 5 are separated as shown in FIG. 4.

In the safety indwelling needle of the present embodiment, the entire inner needle 11 including the needlepoint 12 of the separated inner needle unit 1 is covered by the housing unit 31 and the needle covering member 32 the same as the safety indwelling needle in the first embodiment, and the inner needle unit 1 can be safely discarded. Also, since the extended housing unit 31 cannot be constricted again by the second stoppers 38 provided on the respective housing members 33-35, the needlepoint 12 does not project again, whereby the inner needle unit 1 can be further safely discarded.

Third Embodiment

Figure 5:
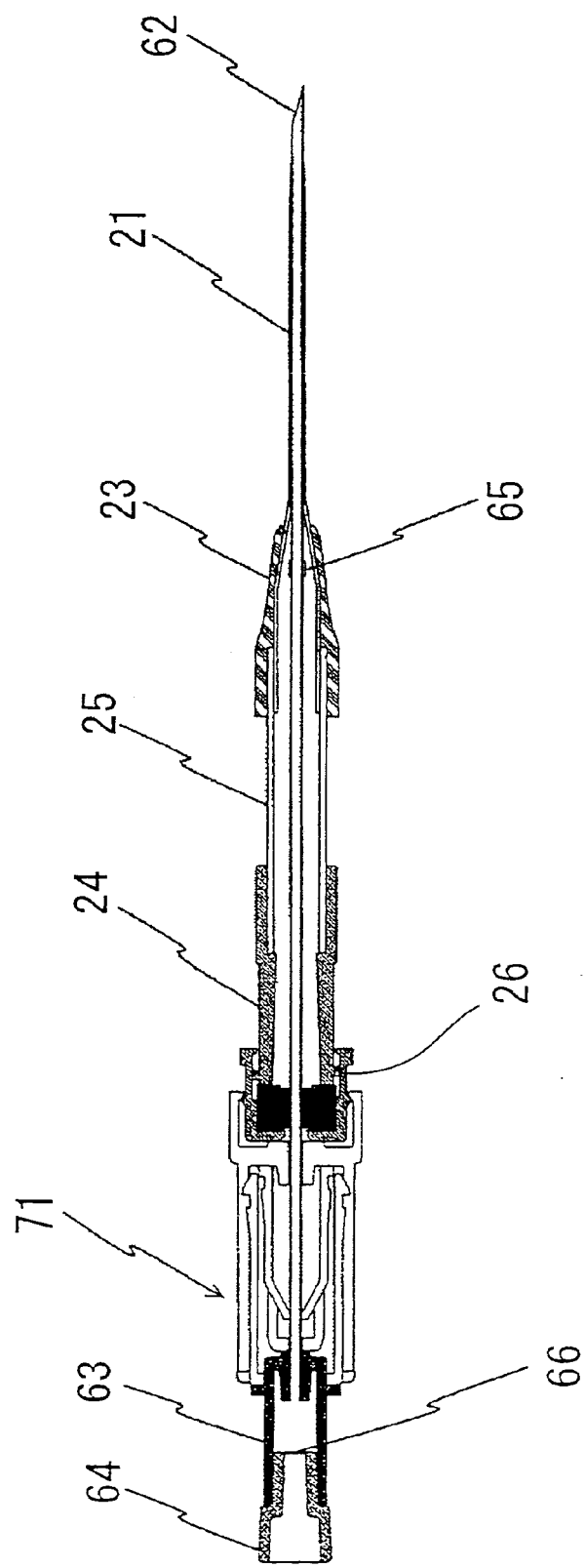
FIG. 5 is a cross-sectional view of the safety indwelling needle according to still another embodiment of the present invention before use.
Figure 6:
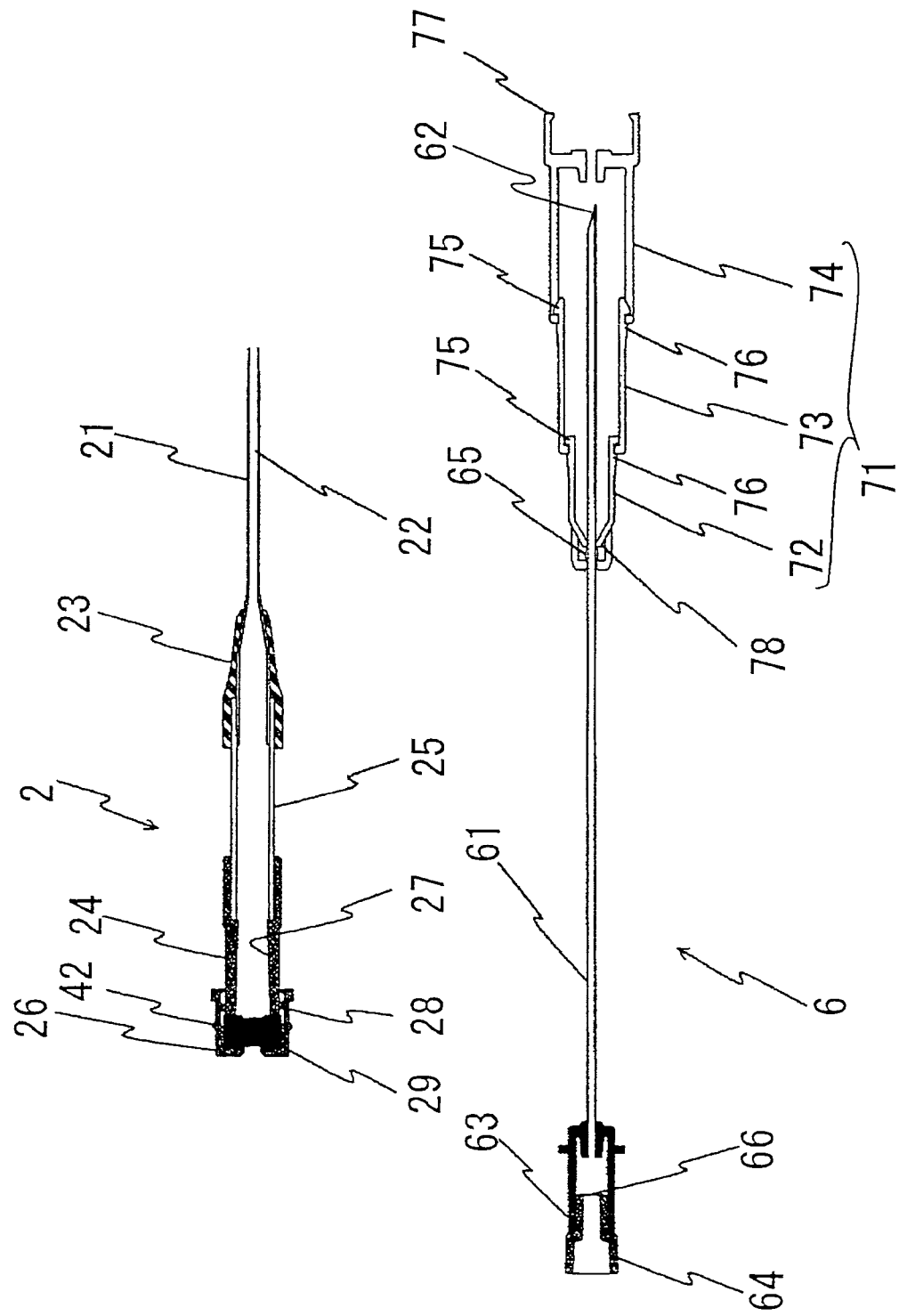
FIG. 6 is a cross-sectional view of the safety indwelling needle shown in FIG. 5 after pulling out an inner needle unit.

The safety indwelling needle according to a third embodiment shown in FIG. 5 and FIG. 6 is mainly used as an indwelling needle especially suitable for a blood purifying therapy such as artificial dialysis. In FIGS. 5 and 6, a structural element of the safety indwelling needle of the third embodiment, which is the same as a structural element of the safety indwelling needle of the first embodiment, is respectively identified using the same reference number as in FIGS. 1 and 2.

The safety indwelling needle shown in FIGS. 5 and 6 includes an inner needle unit 6 and an outer needle unit 2 which is the same as the outer needle unit 2 of the first embodiment. The inner needle unit 6 includes an inner needle 61 having a sharp needlepoint 62 at a distal end and an inner needle hub 63 at a proximal end, and an inner needle cap 64 attached to the inner needle hub 63. In this embodiment, the safety indwelling needle includes a housing unit 71, which is configured as a combination of hollow members including a first housing member 72, a second housing member 73 and a third housing member 74 and extendable in a sliding manner, as a needle protecting member.

The third housing member 74 of the housing unit 71 that is provided on the inner needle unit 6 for storing and covering the needlepoint 62 of the inner needle 61 is detachably connected to the outer needle cap 26 of the outer needle unit 2. The connecting means of the outer needle cap 26 with respect to the third housing member 74 is not specifically limited. However, preferably, the housing unit 71 is extended by an irregular portion on the inner needle 61 while the distal end of the housing unit 71 is connected to the outer needle cap 26 when the inner needle unit 6 is pulled from the outer needle unit 2, and when the housing unit 71 reaches a maximally extended state by first stoppers 76 provided on the respective housing members 72-73 of the housing unit 71, the housing unit 71 comes off from the outer needle cap 26 by further pulling the inner needle unit 6. For example, the third housing member 74 may be detachably connected to the outer needle cap 26 by engaging a flexible hook-shaped member 77 provided on the third housing member 74 to a projecting portion 42 provided on the outer needle cap 26. Alternatively, the hook-shaped member may be provided on the outer needle cap 26 and the projecting portion may be provided on the third housing member 74.

The inner needle 61 is employed the same as the inner needle 11 of the first embodiment. The inner needle 61 is partly formed with an irregular portion on the surface thereof, which is intended for starting an extending operation of the housing unit 71, preventing dropping-out of the housing unit 71 from the inner needle unit 6 and holding the housing unit 71 by a hooking member 78 described later. The irregular portion may be formed, for example, by providing a projection 65 on the circumferential surface of the inner needle 61. The projection 65 may be a doughnut-shaped projection which is entirely provided along the circumference thereof, or one or more projections which is or are partly provided on the circumference thereof.

The positions of the projections 65 must be such that, as shown in FIG. 6, the projection 65 reaches an inner surface on the proximal end in an internal space of the housing unit 71 when the inner needle unit 6 is pulled out from the outer needle unit 2, the housing unit 71 starts extending when the inner needle unit 6 is further pulled, and the needlepoint 62 of the inner needle 61 is completely stored within the housing unit 71 when the housing unit 71 is completely extended.

The projection 65 may be formed at a midsection of the inner needle 61 so that the projection is positioned in an internal space of the outer needle unit 2 in a state in which the inner needle unit 6 and the outer needle unit 2 are assembled and ready to be used for puncturing. Accordingly, since the irregular portion is not positioned in the cavity 22 of the outer needle 21 and a surface of the outer needle 21 is not affected, the projection 65 of the inner needle 61 does not cause any inconvenience when a patient's skin is punctured. Therefore, a relatively large projection 65 may be provided, and hence preventing of drop-out of the housing unit 71 from the inner needle unit 6 and holding of the housing unit 71 by the hooking member 78 can be reliably achieved.

Furthermore, the projection 65 may be formed not in the interior of the outer needle unit 2 but on the proximal side of the inner needle 61. For example, the projection 65 may be provided at a position where the projection 65 resides in the interior of the housing unit 71 at a proximal side from the outer needle 21 in a state before use where the inner needle unit 6 and the outer needle unit 2 are assembled.

The inner needle unit 6 is inserted into the cavity of the outer needle unit 2, and the housing unit 71 through which the inner needle 61 passes is interposed between a distal end of the inner needle hub 63 and a proximal end of the outer needle cap 26 so as to be detachably connected to the proximal end of the outer needle cap 26. The proximal end of the inner needle 61 is secured to the distal end of the inner needle hub 63 in a liquid-tight manner, and a lumen of the inner needle 61 communicates with an internal space of the inner needle hub 63. The inner needle hub 63 is employed the same as the inner needle hub 13 in the first embodiment, and the means of fixing the inner needle 61 and the inner needle hub 63 is the same as the means in the first embodiment. Additionally, a ventilation filter 66 which is the same as the ventilation filter 15 in the first embodiment is preferably provided on the proximal side of the inner needle hub 63.

As shown in FIG. 6, the housing unit 71 according to the present embodiment is composed of a combination of substantially cylindrical hollow members of different diameters (the first to third housing members 72-74), and may be extended in a sliding manner. The housing unit 71 has openings through which the inner needle 61 passes on a distal end and a proximal end. The shape of the opening on the distal end is not specifically limited, but the opening on the proximal end must be of a size which does not allow the projection to pass through, and is preferably substantially a circular shape. The housing unit 71 may be provided with a hard O-ring (not shown) to reliably prevent the inner needle 61 from passing through the housing unit 71. The O-ring is formed of metal or the like and has an inner diameter that is substantially equal to an outer diameter of the inner needle 61, allows the inner needle 61 to pass through and does not allow the projection 65 to pass through. The O-ring is preferably fixed to the interior of the housing unit 71 on the proximal side.

The projection 65 comes into contact with the inner surface of the opening of the housing unit 71 on the proximal end when the inner needle unit 6 is pulled out from the outer needle unit 2, and the slide-type housing unit 71 starts extending when the inner needle unit 6 is further pulled out. At this time, the inner needle 61 provided with the projection 65, which contacts with the inner surface of the opening of the housing unit 71 on the proximal end, is held by the hooking member 78 provided on the housing unit 71 on the proximal end so as not to be relatively moved with respect to the housing unit 71. Then, when the inner needle unit 6 is further pulled out, the housing unit 71 is extended, and when the housing unit 71 reaches a maximally extended state by the first stoppers 75 provided on the hollow members which constitute the housing unit 71, the housing unit 71 is controlled by second stoppers 76 provided on the hollow members so as not to be constricted. The distal side portion of the inner needle 61 from the projection 65 including the needlepoint 62 is covered by the extended housing unit 71.

The connection between the distal end of the housing unit 71 and the outer needle cap 26 is released by further pulling the inner needle unit 6 from a state in which the housing unit 71 is extended to the maximum, and then the inner needle unit 6 and the outer needle unit 2 come off as shown in FIG. 6. The housing members which constitute the housing unit 71 may be provided with a stopper (not shown) which maintains the state in which the housing unit 71 is constricted and releases the state when the housing unit 71 is pulled by a force of a certain degree.

Although the housing unit 71 is composed of a combination of the three hollow housing members 72-74 being different in diameter in FIG. 6, the number of the housing members which constitute the housing unit 71 is not limited. The axial length of the housing unit 71 in the constricted state can be shortened by increasing the number of the housing members. However, employing too many housing members is not preferable because the structure of the housing unit 71 becomes complicated and an outer diameter of the housing unit 71 increases too much. In contrast, when the number of the housing members is reduced, the structure of the housing unit 71 is simplified. However, the total length of the housing unit 71 in a state of being constricted cannot be shortened, thereby the total length of the safety indwelling needle increases.

Although hollow members which increase in diameter toward a distal end are shown in FIG. 6, the indwelling needle of the third embodiment is not limited thereto, and hollow members which decrease in diameter toward the distal end may be used (not shown).

After the safety indwelling needle shown in FIG. 5 is punctured into the skin of a body, the inner needle unit 6 is pulled out from the outer needle unit 2 to obtain the state shown in FIG. 6. At this time, the distal end of the housing unit 71 is connected to the outer needle cap 26 on the outer needle unit 2. Accordingly, when the projection 65 provided on the inner needle 61 reaches the inner surface of the housing unit 71 at the proximal end and the inner needle unit 6 is further pulled out from this position, extension of the housing unit 71 is started. When the housing unit 71 is extended to the maximum extended state defined by the first stoppers 75 and the inner needle unit 6 is further pulled out from this state, the connection between the distal end of the housing unit 71 and the outer needle cap 26 is released, and hence the inner needle unit 6 and the outer needle unit 2 are separated as shown in FIG. 6.

The distal end portion of the inner needle 61 including the needlepoint 62 of the separated inner needle unit 6 is covered by the extended housing unit 71 and the inner needle unit 6 can be safely discarded. Also, the extended housing unit 71 cannot be constricted again because of the second stoppers 76 provided on the housing unit 71, and the inner needle 61 cannot be relatively moved with respect to the housing unit 71 because of the engaging of the projection 65 on the inner needle 61 to the hooking member 78 within the housing unit 71. Therefore, the needlepoint 62 of the inner needle 61 is prevented from projecting from the housing unit 71 again, and hence the inner needle 62 can be covered more safely and more reliably.

Fourth Embodiment

Figure 7:
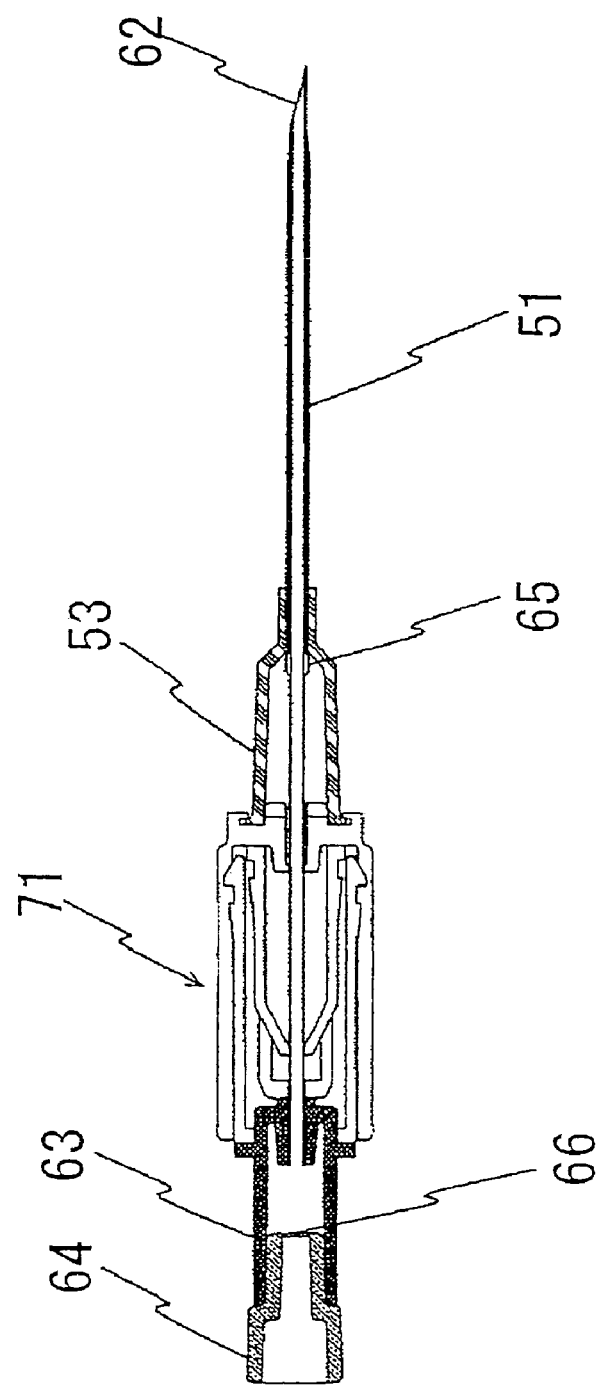
FIG. 7 is a cross-sectional view of the safety indwelling needle according to still another embodiment of the present invention before use.
Figure 8:
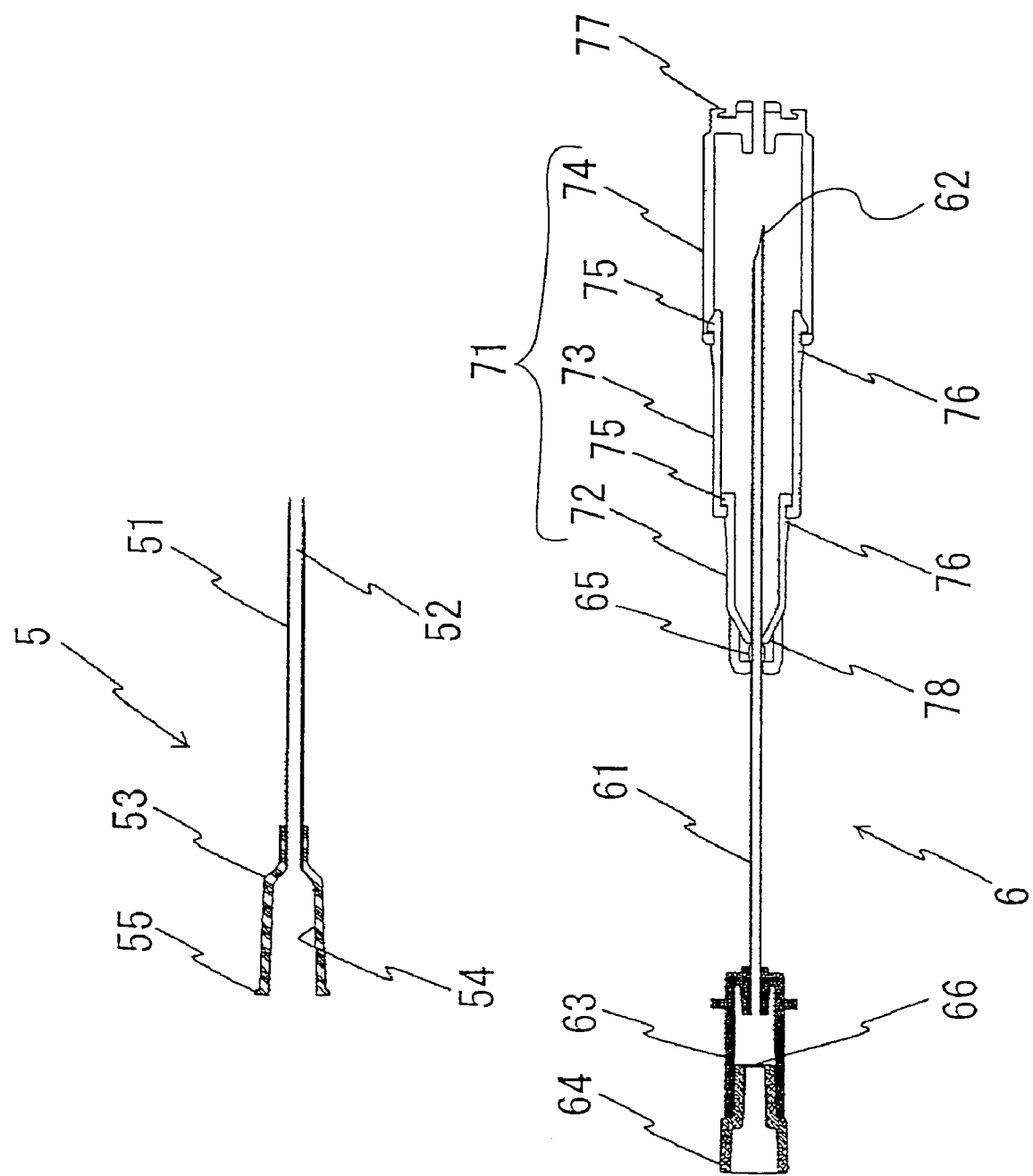
FIG. 8 is a cross-sectional view of the safety indwelling needle shown in FIG. 7 after pulling out an inner needle unit.

The safety indwelling needle according to a fourth embodiment shown in FIG. 7 and FIG. 8 is mainly used as an indwelling needle for fluid infusion or the like. In FIGS. 7 and 8, a structural element of the safety indwelling needle of the fourth embodiment, which is the same as a structural element of the safety indwelling needle of the second or third embodiment, is respectively identified using the same reference number as in FIGS. 3 to 6.

The safety indwelling needle shown in FIGS. 7 and 8 includes an inner needle unit 6 which is substantially the same as the inner needle unit 6 of the third embodiment and the outer needle unit 5 which is the same as the outer needle unit 5 of the second embodiment. The inner needle unit 6 includes inner needle 61 having the sharp needlepoint 62 at the distal end and inner needle hub 63 at the proximal end, and inner needle cap 64 fitted on the inner needle hub 63. In the present embodiment, the safety indwelling needle includes the housing unit 71, which is configured as a combination of hollow members including first housing member 72, second housing member 73 and third housing member 74 and extendible in a sliding manner, as the needle protecting member. The outer needle unit 5 includes outer needle 51 having lumen 52 and outer needle hub 53.

The outer needle hub 53 is detachably connected to the third housing member 74 provided on the inner needle unit 6 for storing and covering the needlepoint 62 of the inner needle 61. The connecting means between the outer needle hub 53 and the third housing member 74 is the same as the connecting means between the outer needle cap 26 and the third housing member 74 in the third embodiment. In the case that the outer needle hub 53 is detachably connected to the third housing member 74 by engaging a hook-shaped member 77 to the projecting portion as described in the third embodiment, the projecting portion may be the locking means 55 provided on the outer needle hub 53.

After the safety indwelling needle shown in FIG. 7 is punctured into a body, the inner needle unit 6 is pulled out from the outer needle unit 5 to obtain the state shown in FIG. 8. At this time, the distal end of the housing unit 71 is connected to the outer needle hub 53 on the outer needle unit 5. Accordingly, when the projection 65 provided on the inner needle 61 reaches the inner surface of the housing unit 71 at the proximal end and the inner needle unit 6 is further pulled out from this position, extension of the housing unit 71 is started. When the housing unit 71 is extended to the maximum extended state defined by the first stoppers 75 and the inner needle unit 6 is further pulled out from this state, the connection between the distal end of the housing unit 71 and the outer needle hub 53 is released, and hence the inner needle unit 6 and the outer needle unit 5 are separated as shown in FIG. 8.

In the safety indwelling needle of the present embodiment, the distal end portion of the inner needle 61 including the needlepoint 62 of the separated inner needle unit 6 is covered by the extended housing unit 71 the same as the safety indwelling needle in the third embodiment, and the inner needle unit 6 can be safely discarded. Also, the extended housing unit 71 cannot be constricted again due to the second stoppers 76 provided on the housing unit 71, and the inner needle 61 cannot be relatively moved with respect to the housing unit 71 due to engaging of the projection 65 on the inner needle 61 to the hooking member 78 within the housing unit 71. Therefore, the needlepoint 62 of the inner needle 61 is prevented from projecting from the housing unit 71 again, and hence the inner needle 62 can be covered more safely and more reliably.

What is claimed is:

1. A safety indwelling needle comprising:
    an inner needle unit which includes an inner needle, an inner needle hub provided on a proximal end of the inner needle, a needlepoint provided at a distal end of the inner needle and a needle protecting member disposed at a distal side of the inner needle hub; and
    an outer needle unit which includes an outer needle having a lumen and an outer needle hub provided on a proximal end of the outer needle,
    said safety indwelling needle being characterized in that the needle protecting member includes an extendable housing unit disposed between a distal end of the inner needle hub and a proximal end of the outer needle unit and being detachably connected to said outer needle unit, said inner needle extending through a distal end of said housing unit and through the lumen of the outer needle in a state in which the housing unit is not extended, the needlepoint of the inner needle being stored in the needle protecting member in a state in which the inner needle is withdrawn from the lumen of the outer needle and the housing unit is extended, and said inner needle being formed with an irregular portion on a surface thereof, which irregular portion engages a proximal end of the housing unit and causes said housing unit to extend as said inner needle is withdrawn from the lumen of the outer needle and the needlepoint of the inner needle to be stored in the housing unit in the state in which the housing unit is extended,
    wherein the housing unit is provided with a hooking member on the proximal end which can be engaged with said irregular portion on the surface of the inner needle so as not to be relatively moved with respect to the housing unit but to extend the extendable housing unit.

2. The safety indwelling needle according to claim 1, wherein the irregular portion on the surface of the inner needle is positioned on a proximal side of the outer needle in a state before use where the inner needle extends through the lumen of the outer needle.

3. The safety indwelling needle according to claim 1, wherein the housing unit is composed of a combination of three housing members which increase in diameter toward a distal end and the housing unit is extended when the irregular portion on the surface of the inner needle reaches the inner surface of the housing unit at the proximal end and the inner needle unit is further pulled from this position.

4. The safety indwelling needle according to claim 1, wherein connection between the distal end of the housing unit and the outer needle cap is released by further pulling the inner needle unit from a state in which the housing unit is extended to the maximum and then the inner needle unit and the outer needle unit come off.

* * * * *